United States Patent
Brcka

(10) Patent No.: US 10,413,913 B2
(45) Date of Patent: Sep. 17, 2019

(54) METHODS AND SYSTEMS FOR DIELECTROPHORESIS (DEP) SEPARATION

(71) Applicant: Tokyo Electron Limited, Minato-ku, Tokyo (JP)

(72) Inventor: Jozef Brcka, Austin, TX (US)

(73) Assignee: Tokyo Electron Limited, Tokyo (JP)

( * ) Notice: Subject to any disclaimer, the term of this patent is extended or adjusted under 35 U.S.C. 154(b) by 110 days.

(21) Appl. No.: 15/433,633

(22) Filed: Feb. 15, 2017

(65) Prior Publication Data

US 2018/0229246 A1    Aug. 16, 2018

(51) Int. Cl.
   *B03C 5/02*    (2006.01)
   *C12M 1/00*    (2006.01)
   *B03C 5/00*    (2006.01)

(52) U.S. Cl.
   CPC .............. *B03C 5/028* (2013.01); *B03C 5/005* (2013.01); *B03C 5/026* (2013.01); *C12M 47/04* (2013.01); *B03C 2201/26* (2013.01)

(58) Field of Classification Search
   CPC ......... B03C 5/028; B03C 5/026; B03C 5/005; B03C 2201/26; C12M 47/04
   See application file for complete search history.

(56) References Cited

U.S. PATENT DOCUMENTS

| | | | |
|---|---|---|---|
| 5,539,609 A | 7/1996 | Collins et al. | |
| 5,820,723 A | 10/1998 | Benjamin et al. | |
| 5,858,192 A * | 1/1999 | Becker | B01J 19/0093 204/280 |
| 5,869,832 A | 2/1999 | Wang et al. | |
| 6,056,861 A | 5/2000 | Fuhr et al. | |
| 7,323,096 B2 | 1/2008 | Yoshida et al. | |
| 7,744,737 B1 | 6/2010 | James et al. | |
| 7,857,952 B2 | 12/2010 | Yoshida et al. | |

(Continued)

FOREIGN PATENT DOCUMENTS

| | | |
|---|---|---|
| DE | 102006023238 A1 | 11/2007 |
| JP | 2010524442 A | 7/2010 |

(Continued)

OTHER PUBLICATIONS

J.O. Hodge, "Experimental Development and Analysis of a Novel Setup for Insulated Dielectrophoresis" Master Thesis, Clemson Univeristy, Aug. 2013.*

(Continued)

*Primary Examiner* — J. Christopher Ball
(74) *Attorney, Agent, or Firm* — Wood Herron & Evans LLP

(57) ABSTRACT

One or more electrodes are attached to an electrically permeable substrate attached to an incubator and energized with A.C. signals, D.C. signals or both A.C. and D.C signals. E-fields emitted from the electrodes pass through the substrate and into the incubator. The e-fields generate or apply dielectrophoresis (DEP) forces on small particles suspended in a liquid inside the incubator. The strength and direction of the DEP forces are controlled and manipulated by the manipulating the signals and can manipulate the motion of the suspended particles. The shapes of the electrodes help shape the generated e-fields and facilitate complex movements of the suspended particles. The suspended particles can be stem cells in a nutrient rich solution.

20 Claims, 17 Drawing Sheets

(56) References Cited

U.S. PATENT DOCUMENTS

| | | |
|---|---|---|
| 7,867,409 B2 | 1/2011 | Brcka |
| 2002/0006360 A1 | 1/2002 | Neal et al. |
| 2002/0063060 A1 | 5/2002 | Gascoyne et al. |
| 2003/0000923 A1 | 1/2003 | Ko et al. |
| 2004/0055891 A1 | 3/2004 | Pamula et al. |
| 2004/0058423 A1 | 3/2004 | Albritton et al. |
| 2004/0096430 A1 | 5/2004 | Bauer |
| 2005/0032204 A1 | 2/2005 | Rodgers et al. |
| 2006/0060303 A1 | 3/2006 | Fink et al. |
| 2006/0115828 A1 | 6/2006 | Palmieri et al. |
| 2006/0228966 A1 | 10/2006 | Gleason et al. |
| 2007/0095669 A1 | 5/2007 | Lau et al. |
| 2007/0125650 A1 | 6/2007 | Scurati et al. |
| 2007/0232076 A1 | 10/2007 | Hori et al. |
| 2007/0281288 A1 | 12/2007 | Belkin et al. |
| 2008/0138797 A1 | 6/2008 | Hunt et al. |
| 2009/0173527 A1 | 7/2009 | Benke et al. |
| 2009/0220865 A1 | 9/2009 | Ouye |
| 2009/0288684 A1 | 11/2009 | Kitaoka et al. |
| 2009/0314644 A1 | 12/2009 | Golan et al. |
| 2009/0325256 A1 | 12/2009 | Yasukawa et al. |
| 2010/0203742 A1 | 8/2010 | Borden et al. |
| 2011/0079513 A1 | 4/2011 | Stelzle et al. |
| 2011/0168558 A1 | 7/2011 | Fransaer et al. |
| 2012/0064567 A1 | 3/2012 | Stakenborg et al. |
| 2012/0135158 A1 | 5/2012 | Freer et al. |
| 2012/0208339 A1 | 8/2012 | Cheng et al. |

FOREIGN PATENT DOCUMENTS

| | | |
|---|---|---|
| TW | 200300464 | 6/2003 |
| WO | 2007116406 A1 | 10/2007 |
| WO | 2008018390 A1 | 2/2008 |
| WO | 2008128717 A1 | 10/2008 |

OTHER PUBLICATIONS

Chen et al., "Aligning single-wall carbon nanotubes with an alternating-current electric field," Appl. Phys. Lett. 78 (23):3714-3716, 2001.

Dimaki et al., "Dielectrophoresis of carbon nanotubes using microelectrodes: a numerical study," Nanotechnology, 15:1095-1102, 2004.

Ho et al., "Rapid heterogeneous liver-cell on-chip patterning via the enhanced field-induced dielectrophoresis trap," Lab Chip, 6:724-734, 2006.

European Patent Office, International Search Report and Written Opinion in corresponding International Application No. PCT/US2012/049056, dated May 17, 2013, 11 pp.

European Patent Office, International Search Report and Written Opinion in corresponding International Application No. PCT/US2012/049040, dated Mar. 6, 2013, 12 pp.

Japan Patent Office, Office Action issued in related Japanese Application No. 2014-524035 dated Mar. 23, 2016; 12 pp.

Taiwan Intellectual Property Office, Examination Opinion in related Taiwanese Patent Application No. 101128013, dated Aug. 25, 2014, 15 pp.

Taiwan Intellectual Property Office, Examination Opinion in related Taiwanese Patent Application No. 101128017, dated Dec. 27, 2014, 15 pp.

European Patenet Office; Office Action in related European Patent Application No. 12753614.2 dated Jun. 13, 2018; 6 pp.

* cited by examiner

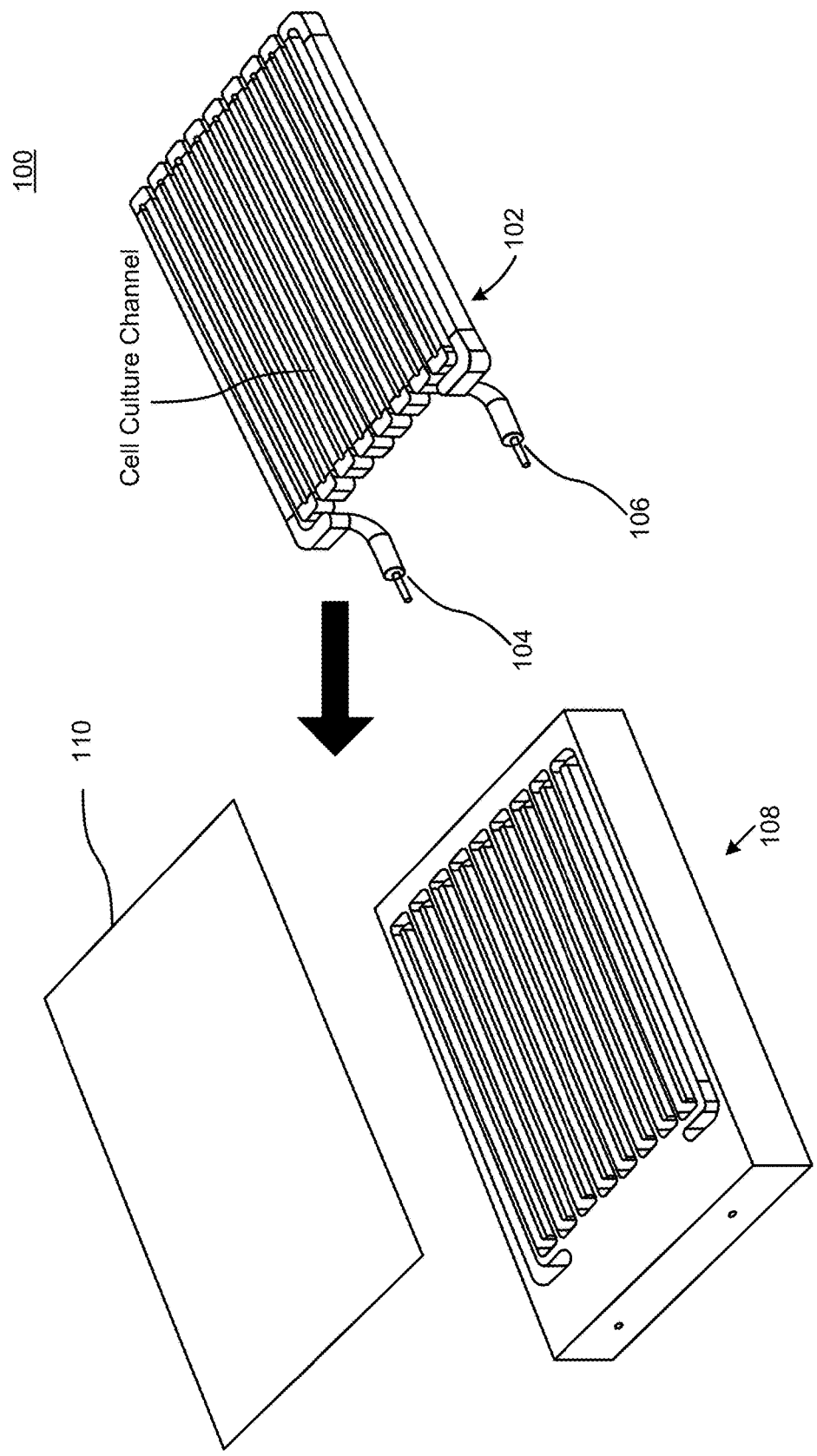

Top View

A-A Cross Section View

| ELECTRODES | POTENTIAL | SYNCHRONIZED BIAS SEQUENCE | SYNCHRONIZED UNBALANCED BIAS SEQUENCE | PROPORTIONAL TW BIAS SEQUENCE AC phase | NON-PROPORTIONAL TW BIAS SEQUENCE AC phase | TW BIAS SEQUENCE AC amplitude and/or temporal modulation |
|---|---|---|---|---|---|---|
| $E_{11}$ | $V_{11}$ | DC or AC | DC or AC | 0 | 0 | $f_1(t)$ |
| $E_{12}$ | $V_{12}$ | ground | DC or AC | $\pi/2$ | $\pi/2$ | |
| $E_{13}$ | $V_{13}$ | DC or AC | DC or AC | $\pi$ | $\pi/2$ | |
| $E_{14}$ | $V_{14}$ | ground | DC or AC | $3\pi/2$ | $\pi$ | |
| $E_{21}$ | $V_{21}$ | DC or AC | ground | 0 | $3\pi/2$ | |
| $E_{22}$ | $V_{22}$ | ground | DC or AC | $\pi/2$ | 0 | |
| $E_{23}$ | $V_{23}$ | DC or AC | DC or AC | $\pi$ | $\pi/2$ | |
| $E_{24}$ | $V_{24}$ | ground | ground | $3\pi/2$ | $3\pi/2$ | |
| $E_{31}$ | $V_{31}$ | DC or AC | DC or AC | 0 | 0 | |
| $E_{32}$ | $V_{32}$ | ground | ground | $\pi/2$ | $\pi/2$ | |
| $E_{33}$ | $V_{33}$ | DC or AC | DC or AC | $\pi$ | $\pi$ | |
| $E_{34}$ | $V_{34}$ | ground | DC or AC | $3\pi/2$ | $3\pi/2$ | |
| $E_{41}$ | $V_{41}$ | DC or AC | DC or AC | 0 | 0 | |
| $E_{42}$ | $V_{42}$ | ground | DC or AC | $\pi/2$ | $\pi/2$ | |
| $E_{43}$ | $V_{43}$ | DC or AC | DC or AC | $\pi$ | $\pi$ | |
| $E_{44}$ | $V_{44}$ | ground | ground | $3\pi/2$ | 0 | |

FIG. 9

| ELECTRODES | POTENTIAL | SYNCHRONIZED BIAS SEQUENCE | SYNCHRONIZED UNBALANCED BIAS SEQUENCE | PROPORTIONAL TW BIAS SEQUENCE AC, phase | NON-PROPORTIONAL TW BIAS SEQUENCE AC, phase | TW$_{EMBASSA}$ BIAS SEQUENCE AC amplitude spatio-temporal modulation |
|---|---|---|---|---|---|---|
| $E_1$ | $V_1$ | DC or AC | DC or AC | 0 | 0 | |
| $E_2$ | $V_2$ | ground | DC or AC | $\pi/2$ | $\pi/2$ | |
| $E_3$ | $V_3$ | DC or AC | DC or AC | $\pi$ | $\pi$ | |
| $E_4$ | $V_4$ | ground | DC or AC | $3\pi/2$ | $3\pi/2$ | $r_i(t)$ |
| $E_5$ | $V_5$ | DC or AC | ground | 0 | 0 | |
| $E_6$ | $V_6$ | ground | DC or AC | $\pi/2$ | $\pi/2$ | |
| $E_7$ | $V_7$ | DC or AC | DC or AC | $\pi$ | $\pi$ | |
| $E_8$ | $V_8$ | ground | DC or AC | $3\pi/2$ | $\pi$ | |
| $E_9$ | $V_9$ | DC or AC | DC or AC | 0 | | |
| $E_{10}$ | $V_{10}$ | ground | DC or AC | $\pi/2$ | | |
| $E_{11}$ | $V_{11}$ | DC or AC | DC or AC | $\pi$ | | |
| $E_{12}$ | $V_{12}$ | ground | ground | $3\pi/2$ | $3\pi/2$ | |

FIG. 10

| ELECTRODES | POTENTIAL | SYNCHRONIZED BIAS SEQUENCE | SYNCHRONIZED UNBALANCED BIAS SEQUENCE | PROPORTIONAL TRVELING WAVE BIAS SEQUENCE AC, phase |
|---|---|---|---|---|
| $E_{11}$ | $V_{11}$ | DC or AC | DC or AC | 0 |
| $E_{12}$ | $V_{12}$ | Ground | DC or AC | $\pi/2$ |
| $E_{13}$ | $V_{13}$ | DC or AC | ground | $\pi$ |
| $E_{14}$ | $V_{14}$ | Ground | DC or AC | $3\pi/2$ |
| $E_{21}$ | $V_{21}$ | DC or AC | DC or AC | 0 |
| $E_{22}$ | $V_{21}$ | Ground | DC or AC | $\pi/2$ |
| $E_{23}$ | $V_{23}$ | DC or AC | ground | $\pi$ |
| $E_{24}$ | $V_{24}$ | Ground | DC or AC | $3\pi/2$ |

FIG. 17

METHODS AND SYSTEMS FOR DIELECTROPHORESIS (DEP) SEPARATION

FIELD OF THE INVENTION

The present invention relates to electrodes used to separate small particles in suspension and which of course includes cells, using dielectrophoresis or "DEP." The present invention also relates to methods for processing cell cultures and cell culture substrates using dielectrophoresis electrode devices.

BACKGROUND

Cells are grown for industrial production purposes in artificial environments under controlled conditions however, growing cells is labor intensive and requires a lot of time. Improving, automating or expending "cell culturing" of induced pluripotent stem cells (iPSC) could have high potential in the fields of cell therapy and regenerative medicine. There is therefore an increasing demand for improved cell culture processes and systems.

One known approach to automate cell growth or cell culturing is to provide or "upload" a large number of cells in suspension into an incubating device in order to expedite growth and thereby produce multiple cell colonies. In that regard, FIG. 1A and FIG. 1B depict a prior art, long-channel incubator 100 used to grow or "culture" cells.

In FIGS. 1A and 1B, an elongated and substantially serpentine-shaped fluid channel 102 provides space wherein individual cells and cell colonies in suspension can grow. An input port 104, which is connected to the channel 102, enables nutrients to be added to the suspension. An outlet port 106 allows cells to be removed or extracted and tests or diagnostics to be performed.

A base plate 108 provides among other things, mechanical support to the culture channel 102. A cover 110 protects the culture channel 102.

Cells in suspension can be added into or "uploaded" into the channel 102 via the input port 104. Conditions for enhanced cell growth in the channel are provided. Such conditions can vary, as those of ordinary skill in the art know and can include exchanging liquids comprising the suspension and providing nutrients to the cells therein. When a cell culture growth ends, the suspension and cells it contains, can be dispensed out of the channel 102.

Despite the assistance provided by incubators, maximizing cell growth and yield for commercial pharmaceutical purposes continues to be expensive, time consuming and difficult. An apparatus and method to improve cell growth would be an improvement over the prior art.

BRIEF DESCRIPTION OF THE DRAWINGS

FIGS. 1A and 1B depict a prior art channel incubator;
FIG. 9 shows values of Table 2;
FIG. 10 shows values of Table 3;
FIG. 17 shows values of Table 1.

DETAILED DESCRIPTION

Figure 2A:
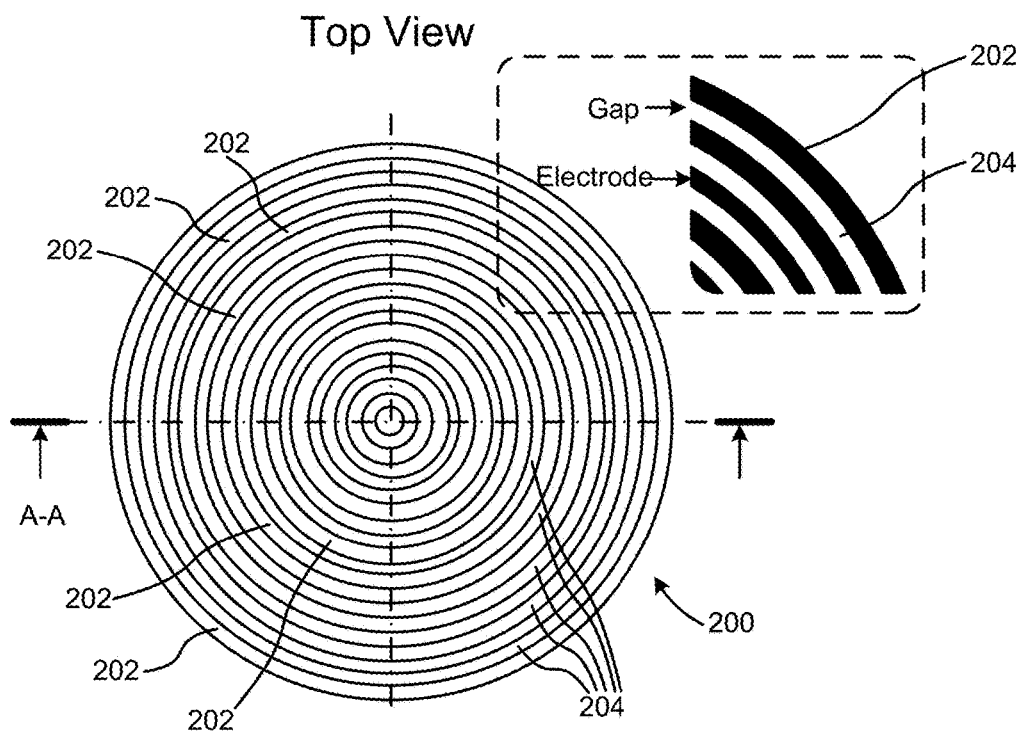
FIGS. 2A and 2B depict top and cross sectional views respectively of a ring-shaped E-field Matrix Assisted Stem Cell Alignment (EMASCA) electrode or electrode device.

Methods and systems for patterning electrodes on electrically permeable substrates are presented herein as are methods for selectively energizing the electrodes in order to manipulate small particles, including stem cells, which are in suspension. One skilled in the relevant art will recognize that the various embodiments may be practiced without one or more of the specific details, or with other replacement and/or additional methods, materials, or components. In other instances, well-known structures, materials, or operations are not shown or described in detail to avoid obscuring aspects of various embodiments of the invention.

Specific numbers, materials, and configurations are set forth in order to provide a thorough understanding of the invention. Nevertheless, the invention may be practiced without specific details. Furthermore, it is understood that the various embodiments shown in the figures are illustrative representations and are not necessarily drawn to scale. In referencing the figures, like numerals refer to like parts throughout.

Reference throughout this specification to "one embodiment" or "an embodiment" or variation thereof means that a particular feature, structure, material, or characteristic described in connection with the embodiment is included in at least one embodiment of the invention, but does not denote that they are present in every embodiment. Thus, the appearances of the phrases such as "in one embodiment" or "in an embodiment" in various places throughout this specification are not necessarily referring to the same embodiment of the invention. Furthermore, the particular features, structures, materials, or characteristics may be combined in any suitable manner in one or more embodiments. Various additional layers and/or structures may be included and/or described features may be omitted in other embodiments.

Additionally, it is to be understood that "a" or "an" may mean "one or more" unless explicitly stated otherwise.

Various operations will be described as multiple discrete operations in turn, in a manner that is most helpful in understanding the invention. However, the order of description should not be construed as to imply that these operations are necessarily order dependent. In particular, these operations need not be performed in the order of presentation. Operations described may be performed in a different order than the described embodiment. Various additional operations may be performed and/or described operations may be omitted in additional embodiments.

As used herein, the term "substrate" means and includes a base material or construction upon which materials are formed. A substrate can include a single material, a plurality of layers of different materials, a layer or layers having regions of different materials or different structures in them, etc. The materials may include semiconductors, insulators, conductors, or combinations thereof. For example, a substrate can be a semiconductor substrate, a base semiconductor layer on a supporting structure, a metal electrode or a semiconductor substrate having one or more layers, structures or regions formed thereon. A substrate can be a conventional silicon substrate or other bulk substrate comprising a layer of semi-conductive material.

An "electrically permeable" substrate is considered herein to be a material through which electric fields can pass readily. Plastics, glass, and most conventional circuit board materials are examples of electrically permeable materials. An "optically transparent, electrically permeable" substrate is a material that allows both visible light and electric fields to pass through it. Plastics and glass are two examples of optically transparent, electrically permeable substrates.

As used herein, the term "bulk substrate" means and includes not only silicon wafers, but also silicon-on-insulator ("SOI") substrates, such as silicon-on-sapphire ("SOS") substrates and silicon-on-glass ("SOG") substrates, epitaxial layers of silicon on a base semiconductor foundation, and other semiconductor or optoelectronic materials, such as silicon-germanium, germanium, gallium arsenide, gallium nitride, and indium phosphide. The substrate may be doped or undoped.

Referring now to the drawings, where like reference numerals designate identical or corresponding parts throughout the several views.

Cell culturing (CC) is a process by which cells from microbes, plants, insects or animal are grown in an artificial environment, such as a channel incubator, a fermenter, bioreactor or other culture container, under controlled conditions. Although the culture conditions can vary widely for different cell types, cell culturing is inherently dependent on specific chemical environments.

The throughput of an artificial environment for cell culturing, as well as its yield are also affected by transport properties within equipment segments. As set forth below, E-field Matrix Assisted Stem Cells Alignment or "EMASCA" is a method of separating growing cells using electric fields (E-fields) on biological cells. EMASCA thus uses dielectrophoresis (or DEP), which is a known phenomenon by which a force is exerted on a dielectric particle when it is subjected to a non-uniform electric field. The DEP-induced force or "DEP force" does not require a particle to be electrically charged.

As is known, particles exhibit dielectrophoretic activity when they are in the presence of electric fields. The strength of the force exerted on a particle depends on many factors, which can include the medium in which a particle is suspended, the particles' electrical properties, the particles' shape and size, as well as on the frequency of the electric field. Consequently, fields of a particular frequency can manipulate different particles with greater or less selectivity. Such selectivity has allowed for cells to be separated using at least their size and orientation. The e-field applied to particles, including cells in a cell culture, can be determined by the size and shape of electrodes from which an e-filed is produced.

As described below, and as shown in the figures, electrically energized electrodes are geometrically sized, shaped and arranged or "configured" to virtually form spatio-temporal distributions of an E-field into specific configurations. Using differently-shaped electrodes to generate or provide DEP forces to cells in order to separate the cells is referred to herein as E-field Matrix Assisted Stem Cells Alignment (EMASCA), or EMASCA force. EMASCA or EMASCA forces can drive, manipulate, propel or otherwise transports cells in an incubator medium to form culture colonies, maintain cells within particular area and/or release cells during unloading process steps.

EMASCA or EMASCA force (used interchangeably hereinafter) is implemented at two levels. First, EMASCA is applied to cell colonies, i.e., acting on individual cells within one colony of cells. EMASCA can thus be used to shaped and maintain a cell colony through several cell culture process steps, such as, improving attachment of cells to a surface, densifying a colony to activate growth, sustaining a colony in place during fermentation and nutrition exchange, separation and detachment from surface at the end of growth process. Second, EMASCA can be applied "in parallel," i.e., on multiple cell colonies to increase the production of cells.

Although conditions of the culture cell process vary widely with type of cells and are inherently dependent on specific chemical environment, the throughput and yield are also affected by their transport properties within equipment segments (incubators, fermenters and bioreactors). Manipulating cells without damage is an important objective for bio-engineering. Disclosed solution is utilizing E-field Matrix Assisted Stem Cells Alignment (EMASCA) method which employs the effect of the electric field (E-field) on biological cells due to a dielectrophoretic force. The EMASCA uses spatio-temporal distribution of the electric field to control cell culture growth process.

Specific time-variant electric field patterns are applied in particular locations of a culture cell incubator. DEP forces move cells into particular areas and cause cell colonies to form in pre-designed structures and shapes and to sustain the cells through growth phase.

DEP provides a way to manipulate cells floating in a liquid medium or suspension. The interaction of electric field with dielectric particle will of course be dependent on uniformity or non-uniformity of an applied electric field as well as cell structure, its shape or size and can be approximated by Equation (1) inset below:

$$F_{DEP} = 2\pi r^3 \varepsilon_m \text{Re}(f_{CM}) \nabla |E|^2 \quad (1)$$

Where
r is a cell radius;
$\varepsilon_m$ is a permittivity of the suspension;
Re($f_{CM}$) is real part of a complex number called Clausius-Mossotti factor; and
E is electric field magnitude.

A dielectrophoretic (DEP) force can be generated using both alternating current (AC) and direct current (DC) electric fields. Dielectrophoretic force acting on a cell and its direction of movement will depend on the applied frequency of an AC current (typically ranging from about 10 kHz to about 100 MHz).

The motion of a cell subjected to DEP force is also complex, due at least in part to interactions between different cells that are subjected to the same DEP force.

Translational or rotational motion of cells can be produced by controlling the phase of an imposed electric field, which will also generate traveling electric waves that will also interact with cells. Novel electrode structures disclosed herein enable cell culturing to be improved or enhanced using DEP forces.

FIG. 2A is a top view of an axis-symmetric ring-shaped electrode device 200, which is deposited onto and thus "attached" to an electrically permeable substrate 206, made from typical materials well known to those of ordinary skill in the art and thus omitted in the interest of brevity. In one other embodiment, the substrate 206 is both electrically transparent and optically transparent, from materials well known in the art, allowing a person or machine to see into the volume where DEP forces are acting on small particles like stem cells.

Figure 2B:
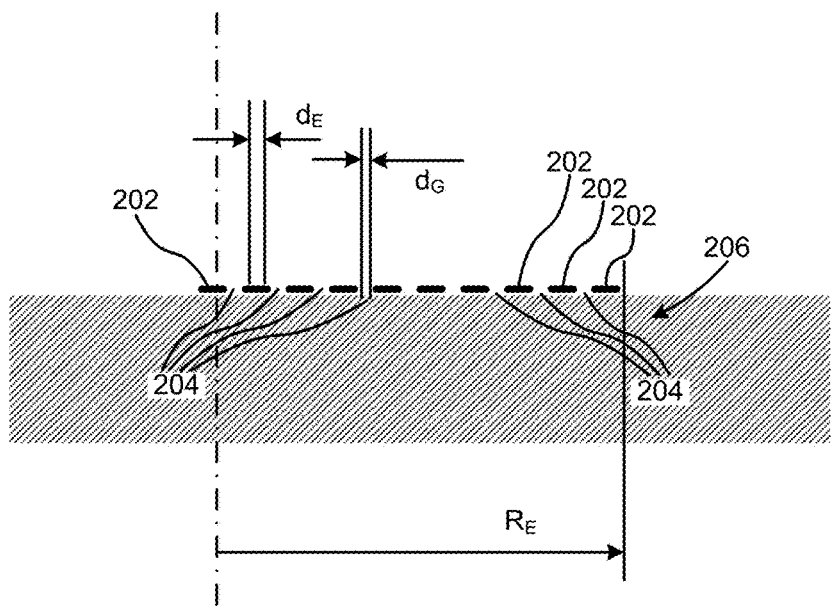
Figure 3A:
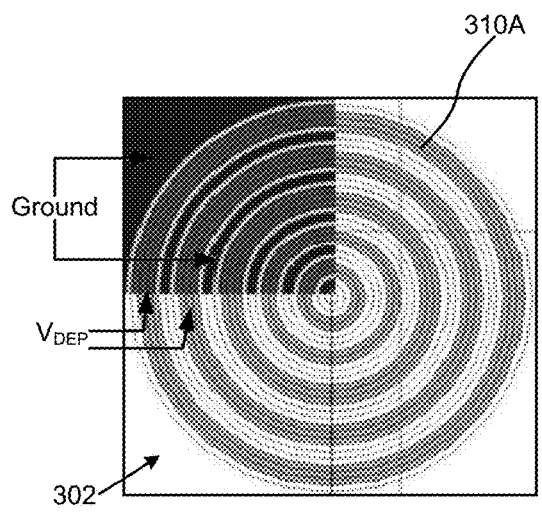
FIGS. 3A-3D depict respectively four (4) ring-shaped EMASCA electrode devices, each of which has a different electrode "width" that is accomplished by applying different electric potentials to the same, ring-shaped electrodes shown in FIGS. 2A and 2B.
Figure 3B:
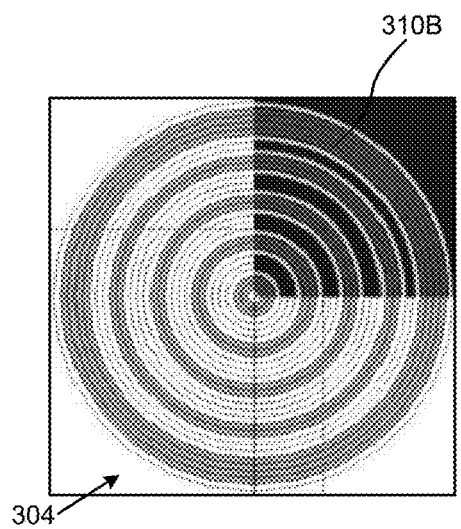
Figure 3C:
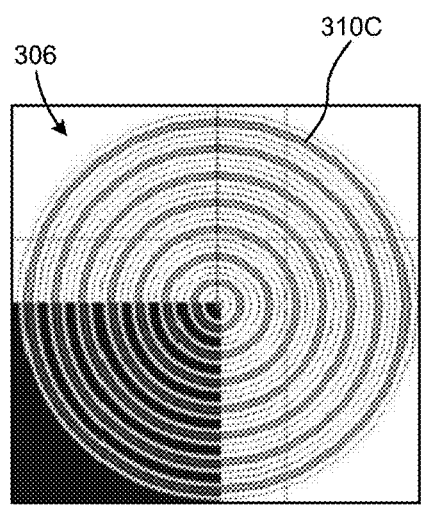
Figure 3D:
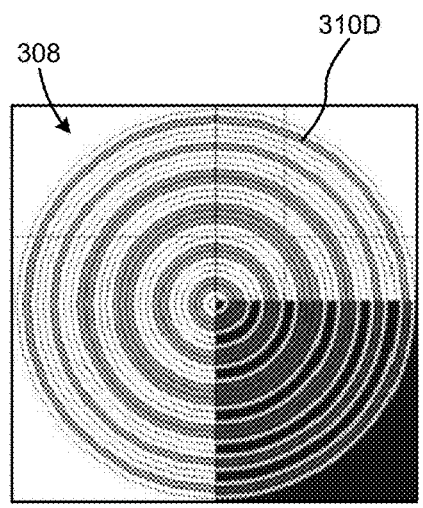

FIG. 2B is a cross-sectional view taken through section lines A-A. Concentric, electrically-conductive ring electrodes 202, each have a nominal width ($d_E$) that preferably ranges from about 20 µm up to about 80 µm in order to accommodate different cells of different sizes, especially differ-sized stem cells. Electrically energizing the ring-shaped electrodes 202 shown in FIG. 2A enables different cells to be aligned along the electrodes' width, $d_E$.

A gap 204 separates the electrodes 202 electrically. The gaps size ($d_G$) or separation distance is preferably much smaller than the electrodes' width and preferably between about 5 µm up to about 20 µm.

The electrodes 202 are energized with either DC signals, AC signals or a combination of both. Electrode 202 and gap 204 dimensions are selected responsive to stem cell sizes, which are typically about 10 µm up to about 15 µm. Electrode and gap dimensions can of course be scaled appropriately to the sizes of various different-size stem cells.

The overall size of single EMASCA embodiment is accommodated to optimal size of cell culture colony. A colony is a collection of cells that has an area of several millimeters and typically within a 3×3 mm² area.

The EMASCA electrode structure/electrode device 200 shown in FIGS. 2A and 2B is created on one side of a dielectric cover plate 206, which can also be the substrate that supports EMASCA electrodes. The electrode material can be deposited by an appropriate technique including but not limited to vapor deposition and patterning techniques.

The cover plate 206 carrying the electrode can be positioned over a suspension liquid in an incubator at least two different ways. Electrodes 202 can face "downward" and thus close or "adjacent" to a suspension liquid, not shown. The electrodes on a cover plate 202 can also face "upward" or away from a suspension, as shown in FIG. 2B such that an E-field will nevertheless pass through the cover 206. EMASCA electrodes 202 can also be embedded into a cover.

For in-situ diagnostic purposes, it is preferable to have electrodes 202 that are made of an optically transparent material such as indium tin oxide (ITO) and applied to a similarly transparent material, such as polystyrene.

It is also preferable that electrodes 202 not make contact with either a suspension liquid or cells therein. Thus, a thin coating of insulating material is optionally deposited over the electrode structures that "face" downwardly, i.e., adjacent to a liquid solution. The thickness of such a coating is preferably in a range extending from about 100 nm up to about 1 µm.

Still referring to FIGS. 2A and 2B, various benefits of the equidistant electrode 202/gap 204 series include arranging or selecting the dimensions of the electrode 202 and gap 204 using a formula or algorithm for electrical potentials.

FIGS. 3A-3D respectively illustrate four (4) different electrode devices 302, 304, 306 and 308, but which have the same electrode structure. The various quadrants depicted in the corresponding figures represent the electrically different fields 310A-310D accomplished by different electric potentials applied to the individual electrodes 202 shown in FIGS. 2A and 2B, thereby forming "virtual electrodes," which have an "effective" width, that varies according to the potentials the actual electrodes 202 carry.

A.C. potentials applied to the electrodes 202 can vary in magnitude and frequency. D.C. potentials can vary in magnitude. The potentials applied to the electrodes 202 can also include multiple different A.C. signals, at two or more different frequencies, two or more different amplitudes and which can be modulated by frequency, phase relative to each other, and amplitude. The electrodes that appear to be larger do so because they carry larger or different potentials and thus generate a larger or different spatial distribution of an induced electric field.

Figure 4A:
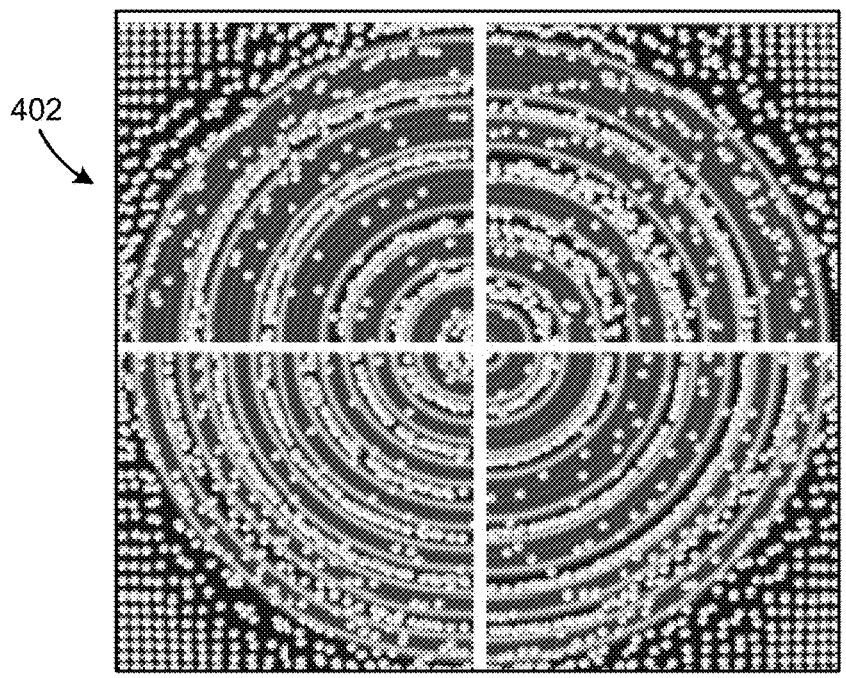
FIGS. 4A and 4B respectively show patterns of stem cells above the surfaces of the electrodes shown in FIGS. 3A-3D, each quadrant shown in the figures representing corresponding ones of the four (4) different electrode configurations shown in FIGS. 3A-3D.
Figure 4B:
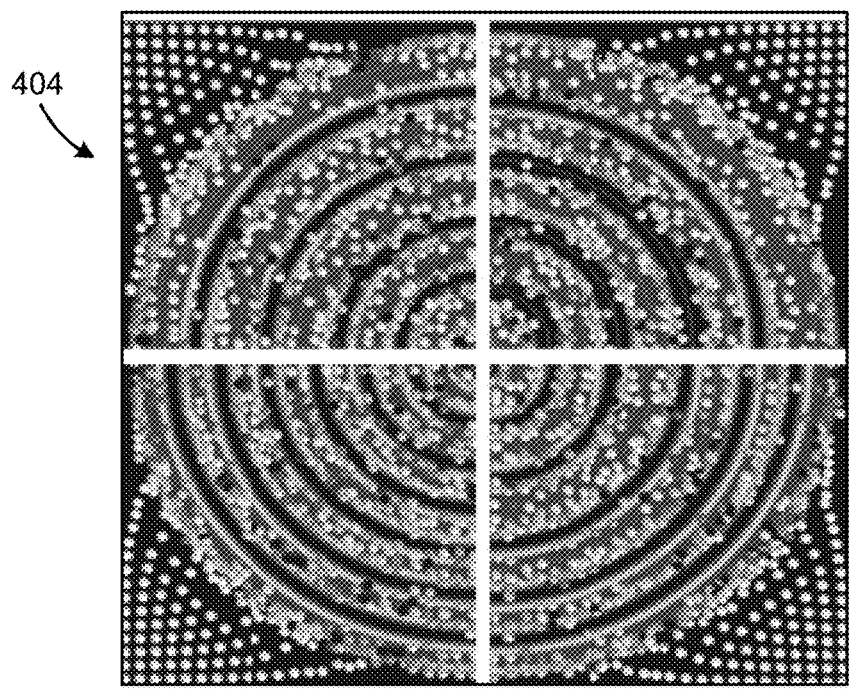

The "virtual widths" of the electrodes depicted in FIGS. 3A-3D, are determined or provided by a biasing algorithm. Different electric fields between electrodes are due to a pre-programmed bias patterning. In the case of a "negative" or repulsive DEP, cells are pushed away from or repulsed from an electrode into the pattern 402 shown in FIG. 4A. In the case of a "positive" DEP, cells are attracted or pulled to an electrode into a different pattern 404, such as the one shown in FIG. 4B. As with a negative DEP, cell pattern is determined by electric fields.

Figure 5A:
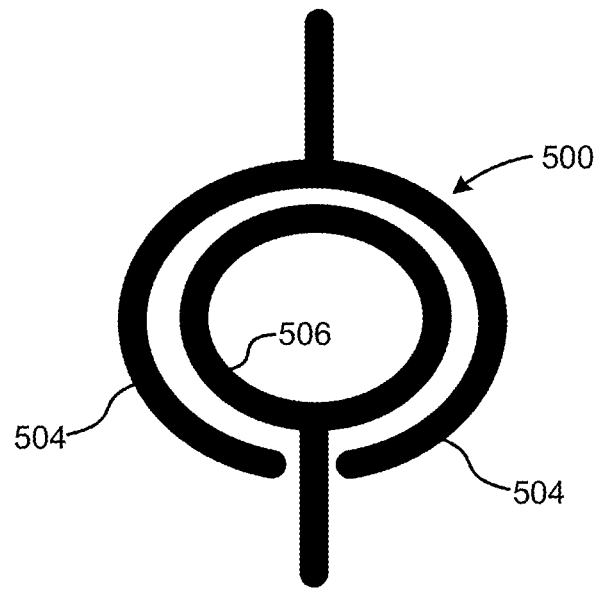
FIGS. 5A and 5B respectively depict top views of electrode devices having two different embodiments of interdigitated electrodes or simply, "IDEs.
Figure 5B:
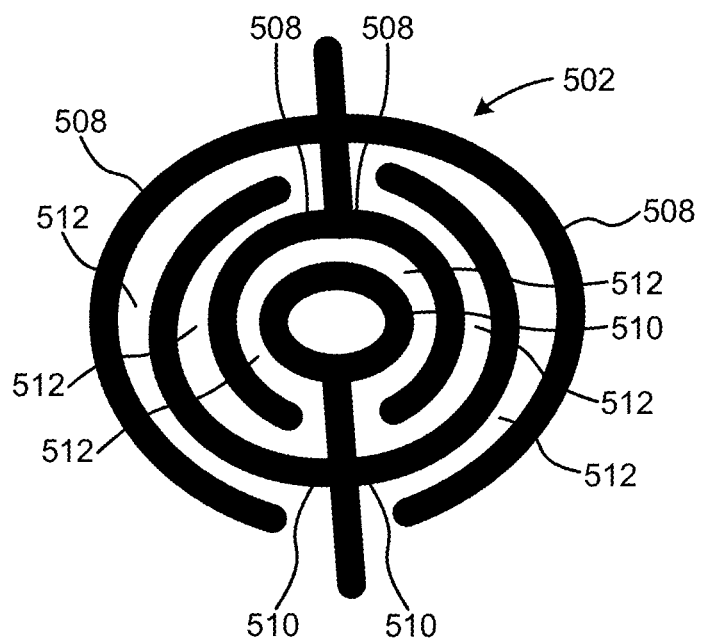

Merriam-Webster's Collegiate Dictionary defines the verb "interdigitate" as meaning "interlocked like the fingers of folded hands. FIGS. 5A and 5B depict top views of EMASCA electrode devices 500, 502 respectively, formed by interdigitated concentric (IDEs) electrodes 504, 506 and 508, 510 respectively and gaps 512.

Referring now to FIG. 5A, a single loop 504, is essentially surrounded by an outer ring 506. In FIG. 5B, multiple loops 508 at a first electric potential are surrounded by "mating" loops, which are at a different electric potential. The loops 508, 510 are considered herein to be interdigitated. Other rectangular, hexagonal or polygonal shapes can also be used to provide electrode devices that are also interdigitated.

(FIG. 6) depicts a top view of an electrode configuration referred to herein as a "2H4" electrode configuration 600. The 2H4 embodiment 2H4 comprises of two sets of congruent electrodes 602, 604, 606, 608, 610, 612, 614 and 616 with gaps 618.

Figure 7:
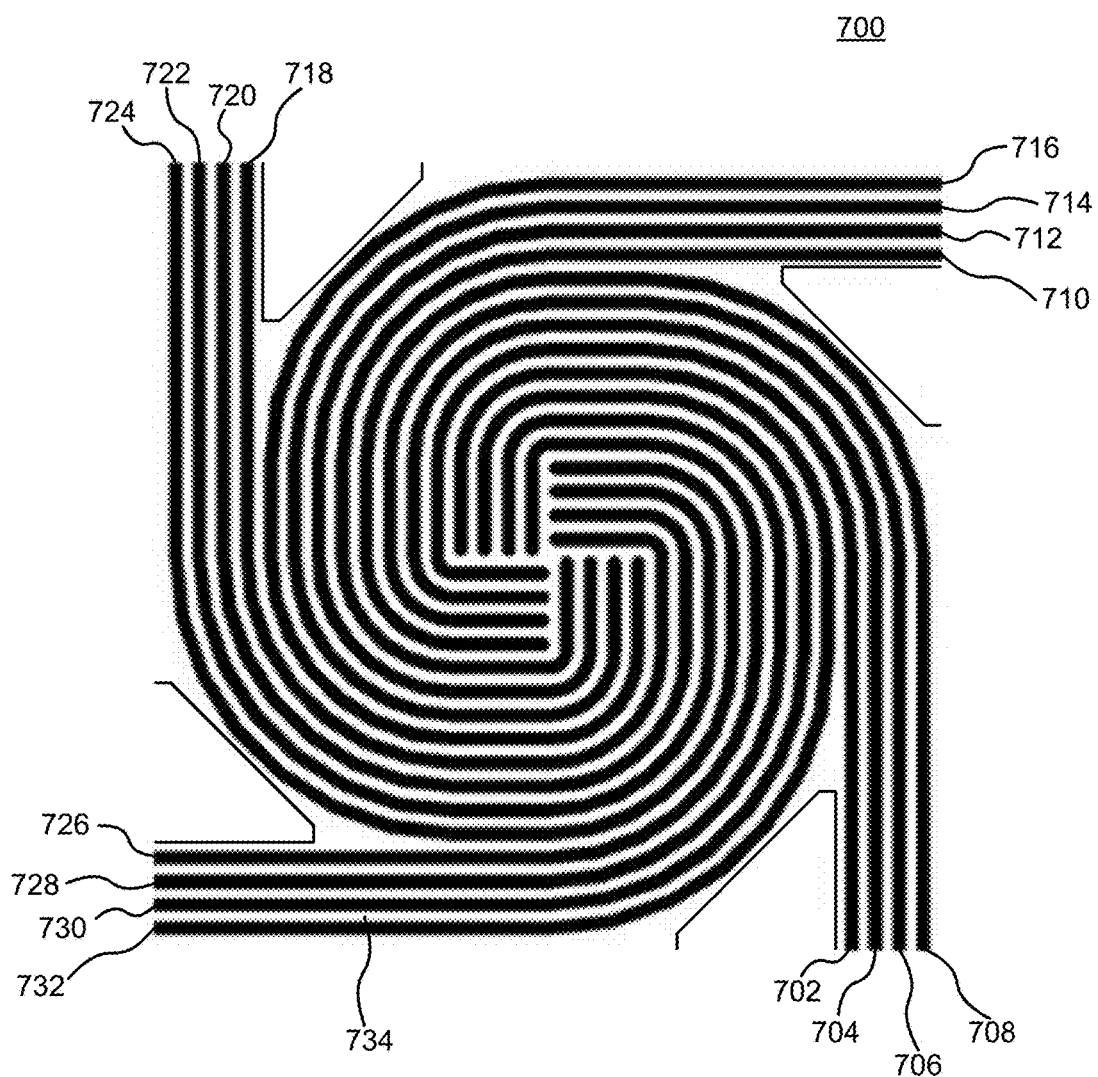
FIG. 7 is top view of a "4Q4" EMASCA electrode device, comprising congruent, spiral-like electrodes with quadrant symmetry.

FIG. 7 is top view of the applicant's "4Q4" EMASCA electrode device 700. It comprises four sets of electrodes each set being composed of at least four electrodes 702-732.

Figure 8:
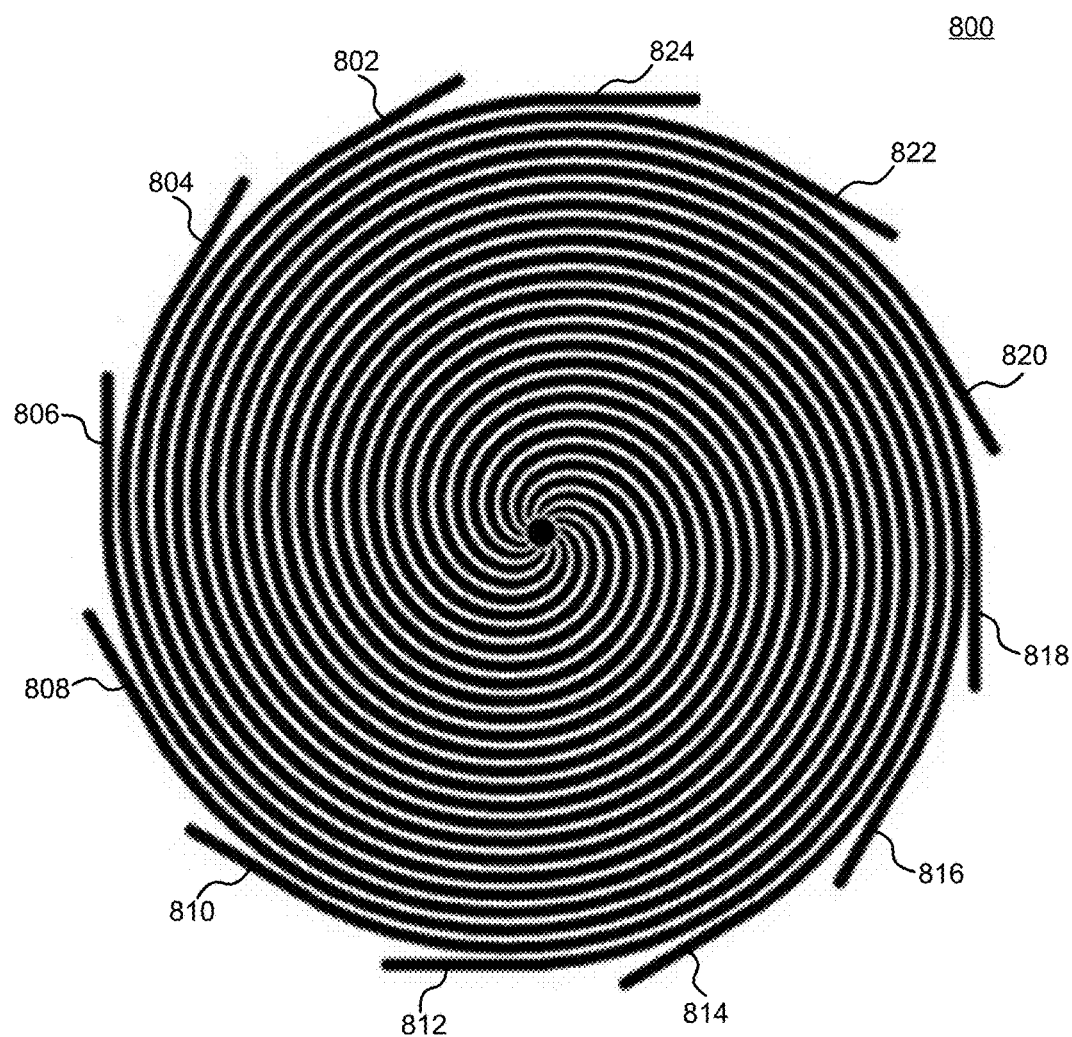
FIG. 8 is a top view of the "MS 12" EMASCA electrode device, which comprises congruent, Archimedean-spiral-like electrodes.

FIG. 8 is a top view of the applicant's "MS 12" EMASCA electrode device 800. It comprises multiple congruent, Archimedean-spiral-like electrodes 802-814. Congruent spiral electrodes provide a spiral shape having a curvature that increases, i.e., the radius decreases continuously, which provides an electric field having a gradient that is increased azimuthally. This will produce azimuthal component to E-field and its gradient, especially when width of electrodes and gaps is reduced with smaller radius.

Figure 6:
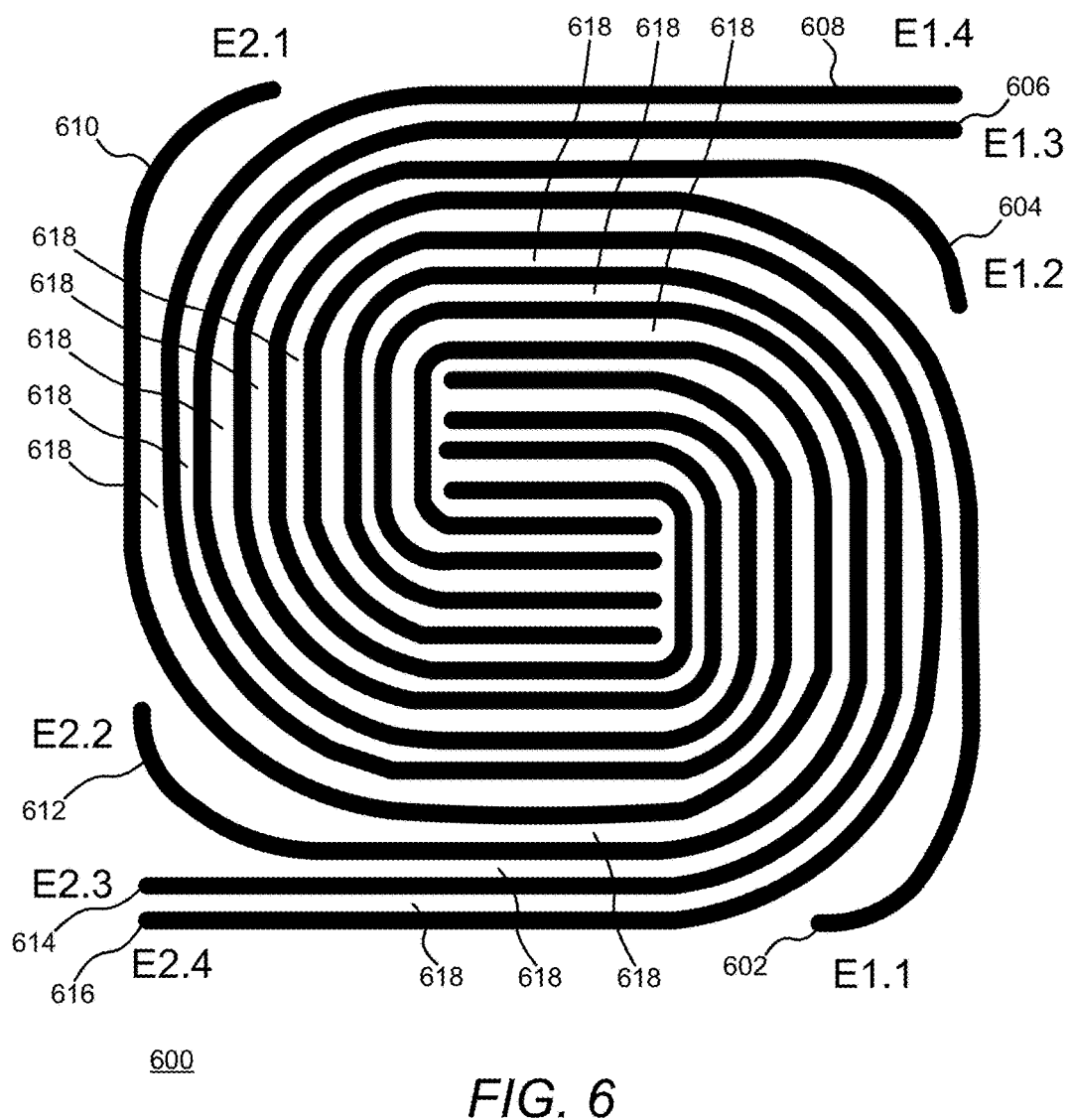
"
FIG. 6 is a top view of an electrode configuration referred to herein as a "2H4" electrode configuration and which comprises congruent, substantially spiral-shaped electrodes.

Each of the electrode devices 600, 700 and 800 shown in FIGS. 6, 7 and 8 respectively, can "shape" or "direct" an electric field and thus shape or direct a DEP force by appropriately driving the non-rectilinear conductors with time and/or amplitude-varying electric fields. Shaping a DEP force can thus be used to direct or urge small particles, including stem cells, around a volume or an area simply by manipulating the e-fields provided to various electrodes.

Table 1, which is depicted in FIG. 17, provides spatial-temporal configurations for the 2H4 EMASCA setup and electrode devices as shown in FIG. 6.

Tables 2 and 3, which are depicted in FIGS. 9 and 10 respectively, provide spatial-temporal configurations for the 4Q4 EMASCA electrode devices shown in FIG. 7 and the MS12 EMASCA electrode device shown in FIG. 8 respectively.

The EMASCA electrodes with multiple electrodes can be successfully used with a traveling wave algorithm that requires at least four independent and congruent electrodes. Each set contains at least four electrodes separated by narrow gaps, which means they are electrically insulated each from the other.

Figure 11A:
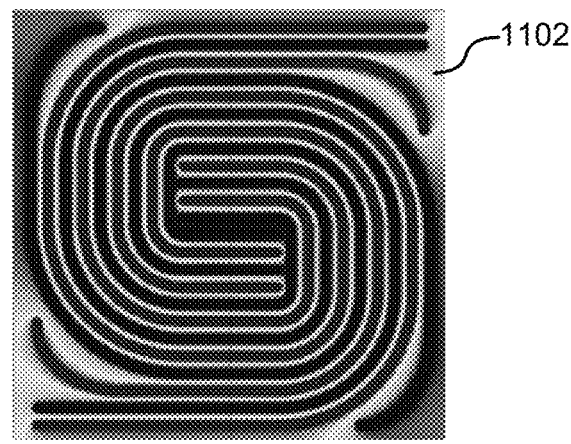
FIG. 11A depicts an e-field generated from the electrode device depicted in FIG. 6
Figure 11B:
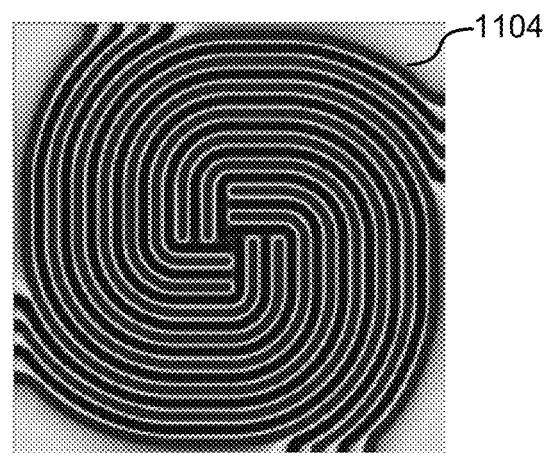
FIG. 11B depicts an e-field generated from the electrode device depicted in FIG. 7.
Figure 11C:
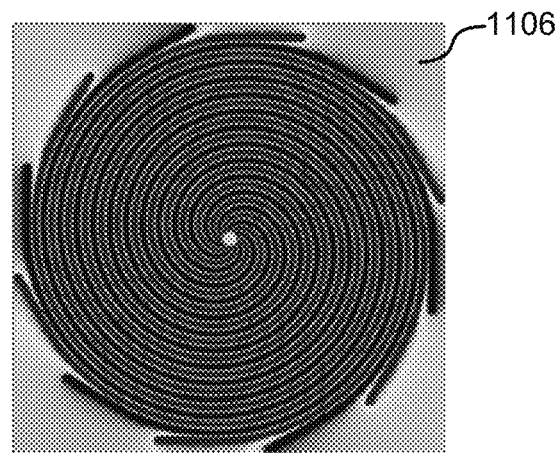
FIG. 11C depicts an e-field generated from the electrode device depicted in FIG. 8.

FIG. 11A depicts an e-field 1102 generated from the electrode device depicted in FIG. 6. FIG. 11B depicts an e-field 1104 generated from the electrode device depicted in FIG. 7. FIG. 11C depicts an e-field 1106 generated from the electrode device depicted in FIG. 8. The e-fields 1102, 1104 and 1106 are different in magnitude and shape, due in large part to the differently-shaped electrodes from which they are emitted. Spatial resolution for steering small particles or stem cells is also assisted when an appropriately-selected voltage potential is applied to the various electrodes sequentially, and which is shown in the third column of Tables 1, 2, and 3.

In Table 1, provided in FIG. 17, and Tables 2 and 3 provided in FIGS. 9 and 10, one grouping combination of the electrodes under the same potential or ground is demonstrated. Other grouping combinations are possible.

The fifth columns in Tables 1, 2 and 3 describes a "TRAVELING WAVE BIAS SEQUENCE," which can be formed by phasing-out individual electrodes by π/2. At least four electrodes are necessary to form traveling wave on congruent electrodes. Implementing electrode subsets with four or more subsets enables a travel wave to be created across the congruent electrodes, and that can be arranged by at least four sinusoidal potentials with phase shift π/2. A traveling wave propagates radially or toward the center of a cell colony. An AC potential on single subset of electrodes, can be represented by the equations for phase-out given by expressions.

$$V_{E1} = V_{0E1} \sin(\omega_{DEP} t) \quad (2\text{-}A)$$

$$V_{E2} = V_{0E2} \sin(\omega_{DEP} t + \pi/2) \quad (2\text{-}B)$$

$$V_{E3} = V_{0E3} \sin(\omega_{DEP} t + \pi) \quad (2\text{-}C)$$

$$V_{E4} = V_{0E4} \sin(\omega_{DEP} t + 3\pi/2) \quad (2\text{-}D)$$

where $V_{0E1}$, $V_{0E2}$, $V_{0E3}$ and $V_{0E4}$ represent the amplitudes of an AC field applied to the electrodes, and $\omega_{DEP} = 2\pi f_{DEP}$ is an angular frequency of an applied AC field at frequency $f_{DEP}$.

When a large number of the electrodes are implemented in an EMASCA electrode device, more than four electrodes can be used to create either proportional or non-proportional traveling waves across the congruent electrode devices. For example, the 2H4-EMASCA configuration (FIG. 6 and Table 1) allows a proportional traveling wave (TW) wave but it is not feasible to implement a non-proportional traveling wave due to the fact, that four electrodes are involved to complete motion along the radius. Larger number of electrodes is therefore preferred.

The 4Q4-EMASCA (FIG. 7 and Table 2) and MS12-EMASCA (FIG. 8 and Table 3) configurations allow both proportional and non-proportional traveling waves (TW). Non-proportional TW sequence provides conditions to apply either narrow or wider virtual electrode EMASCA concept. A bias sequence is shown in the sixth column of Tables 2 and 3. Furthermore, a limitation of the phasing-out electrode potentials according equations (2) is that velocity of the radial propagation of the TW, $v_{TW}$, is related to operational frequency of the electric field:

$$v_{TW} = 4 f_{DEP} (d_E + d_G) \quad (3)$$

Operational frequency is chosen from the viewpoint of the DEP force to be imposed on stem cells, which is determined by electrical properties of stem cells and liquid suspension. See Eq. 1. Such frequency may not be always optimal from viewpoint of physical motion and manipulation with stem cell on the surface.

There is a benefit to separate transport and patterning of the stem cells using a dielectrophoretic force from spatio-temporal control of electric field. To arrange that, it is necessary to apply additional spatio-temporal modulation of the E-field.

Figure 12:
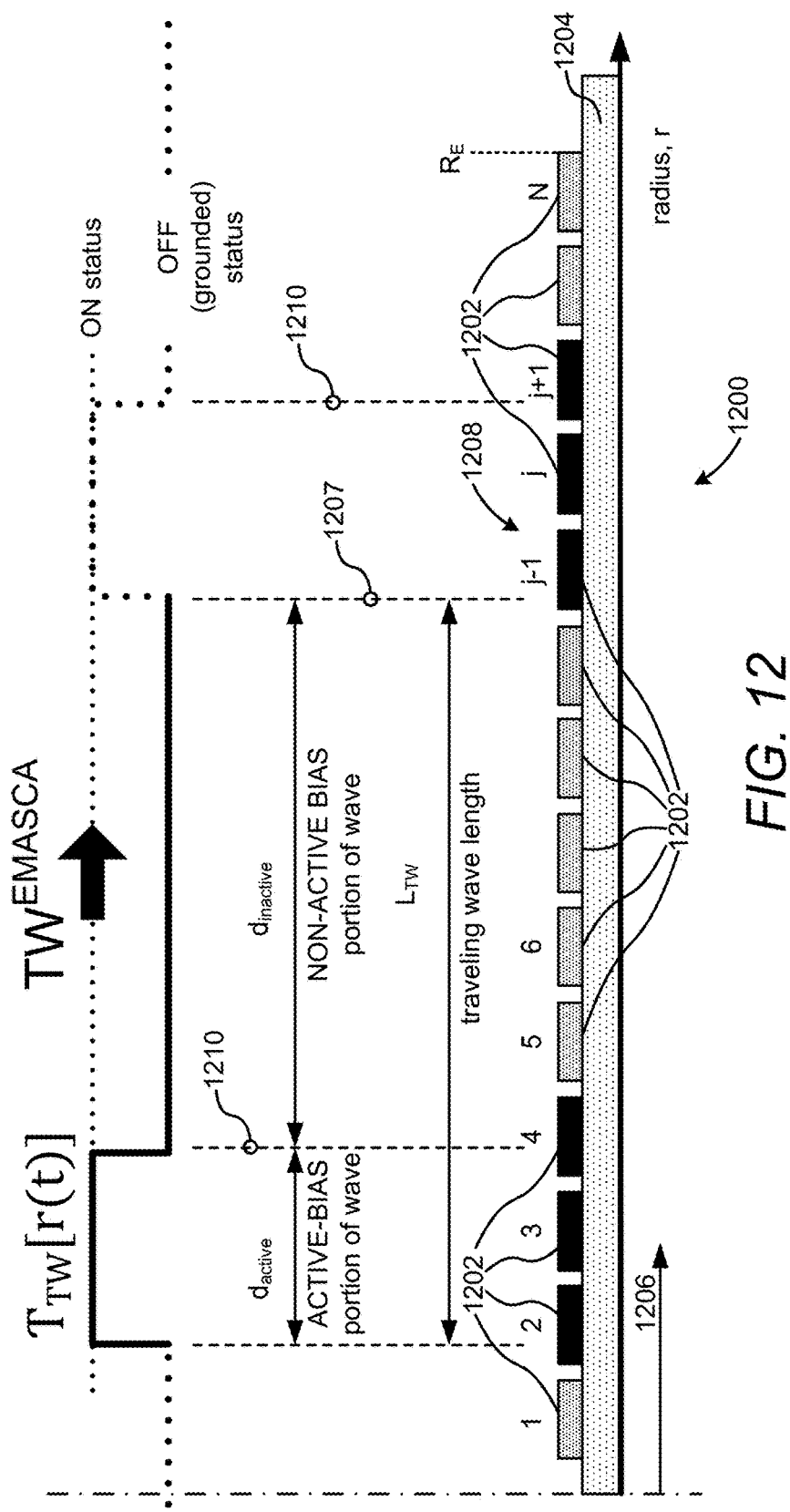
FIG. 12 shows an EMASCA spatio-temporal modulation.

FIG. 12 shows the cross-section of an EMASCA electrode device 1200. Electrodes 1202 are formed on a substantially planar surface of an electrically transparent substrate 1204.

In the radial direction 1206 there is a sequence of multiple electrodes (N) 1202. Spatio-temporal distribution of the E-field and its gradient nearby the surface is formed by AC potentials, which generate a DEP force. A moving E-field pattern 1207 is generated on the surface 1208 of the electrodes 1202 according to an expression that generates at least one region or zone 1210 where the potential between two electrodes 1202 is in transition from active/energized to non-active/de-energized status, and its propagation is arranged through biasing different groups of electrodes 1202.

Input parameters for an TW$^{EMASCA}$ algorithm are velocity ($v_{TW}^{EMASCA}$) of a traveling wave or in other terms it is traveling wave frequency, $f_{TW}$, since these are related by equation 4 bellow.

Figure 13:
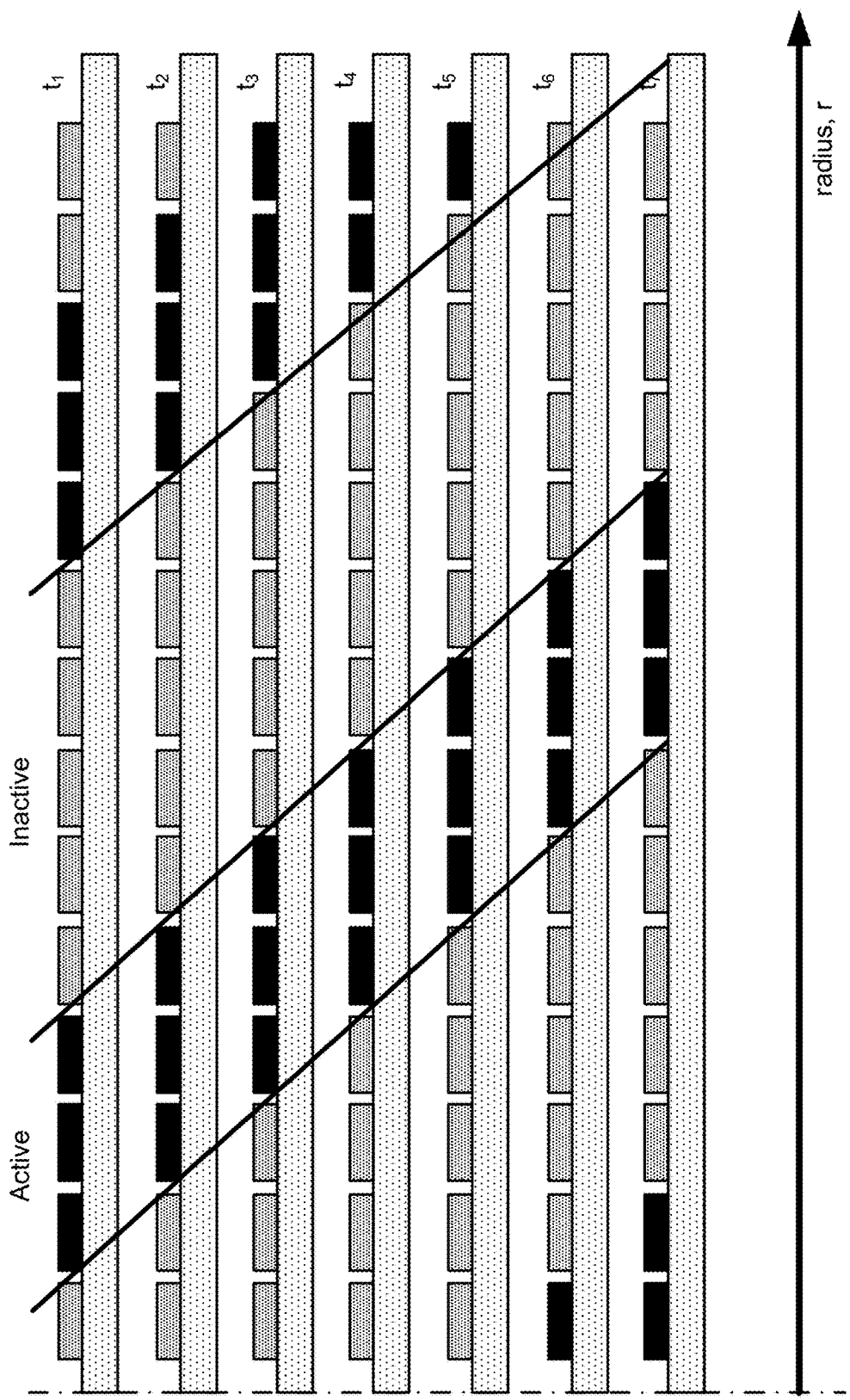
FIG. 13 shows a traveling wave based on the EMASCA concept—outwardly propagation through congruent multi-electrodes configuration.

Mathematically, a non-proportional TW within EMASCA system with N-electrodes and can be formed according to the independent relationship between electric field frequency, $f_{DEP}$, and TW frequency, $f_{TW}$. Assuming that traveling wave frequency is $f_{TW} = v_{TW}^{EMASCA}/R_E$, a moving rectangular wave can be created where each electrode numbered $n_E = 1, 2, 3, \ldots, j-1, j, j+1, \ldots N$, is biased by a dielectrophoretic potential equal to $V_{AC} = V_0 e^{i\omega_{DEP} t}$ with a frequency $f_{DEP}$ under the condition that it is activated on $j^{th}$-electrode according the following equation 4:

$$\Gamma_j(t) = \text{sign}(\{\text{sign}[\sin(\pi f_{TW} t \pm (j-1)\Delta\varphi)] + 1\} \times \{\text{sign}[-\sin(\pi f_{TW}(t - t_{active}) \pm (j-1)(\Delta\varphi)] + 1\}) + + \text{sign}(\{\text{sign}[\sin(\pi f_{TW} t + \pi \pm (j-1)\Delta\varphi)] + 1\} \times \{\text{sign}[-\sin(\pi f_{TW}(t - t_{active}) + \pi \pm (j-1)\Delta\varphi)] + 1\}) \quad (4)$$

where ± sign in the front of phase member indicates forward or backward travel wave, $\Delta\varphi = \pi R_e/(L_{TW} N)$ and active time $t_{active}=d_{active}/(R_E f_{TW})$ indicates duration of applied AC potential. Spatio-temporal potential at EMASCA electrode system will be given then by expression:

$$V(j,t)=\Gamma_j(t)_{0j}e^{i\omega_{DEP}t} \quad (5)$$

where $V_{0j}$ stands for amplitude applied at $j^{th}$-electrode and other symbols have previous meaning. This time-dependent function has value between 0 and 1. The bias sequence in increasing time will look substantially as illustrated in FIG. 13 and the implementation formulated in the seventh column in Tables 2 and 3.

Such an approach will form an electric field between several electrodes ($N_{E1}$) biased at one potential and several electrodes ($N_{E2}$) at the second potential. Such electric field distribution should propagate radially, to or from the center of stem cell colony.

The parameters, $N_{E1}$ and $N_{E2}$, will determine a virtual width of EMASCA electrodes. The parameters $d_E$ and $d_G$ represent size of the physical electrodes in disclosed embodiments. Products $N_{E1}(d_E+d_G)$ and $N_{E2}(d_E+d_G)$ represent a virtual electrode formation that is given by appropriate algorithm.

Equations (2) and (4) will form complex distribution of the electric field with propagation towards (or out of) the center of stem cell colony. Cells in liquid medium will be forced to propagate with E-field and its gradient, $\nabla E(x,y,z,t)$ due to the dielectrophoretic force induced by E-field on the stem cells. Results of the numerical models confirm such motion. Further knowledge of performance and optimal operation can be gained from experimentation with EMASCA system.

Equation (4) is derived from a mathematical interpretation of periodic rectangular function (See FIG. 12) to create proper conditions for a spatio-temporal distribution of the E-field for stem cells alignment. Another mathematical interpretation or formula can be derived or SW programming means (language, coding) used to describe such function, new function might be smoother, without sharp corners or combination (superposition) of multiple quasi-rectangular functions can be used, however, these variation will not change the concept of this disclosure.

As described above DEP forces generated by changing e-fields from the EMASCA electrodes in FIGS. 2, 5 6, 7 and 8, will act on the individual cells within one colony, helping to provide or located the cells for optimal collection, maintain growth process and enable their release from a surface. Such an arrangement is multiplied within or by the cell culture plate into an array or matrix configuration when the EMASCA electrodes are distributed on the surface of cell culture plate, such as the cell cover plate shown in FIG. 1.

Figure 14A:
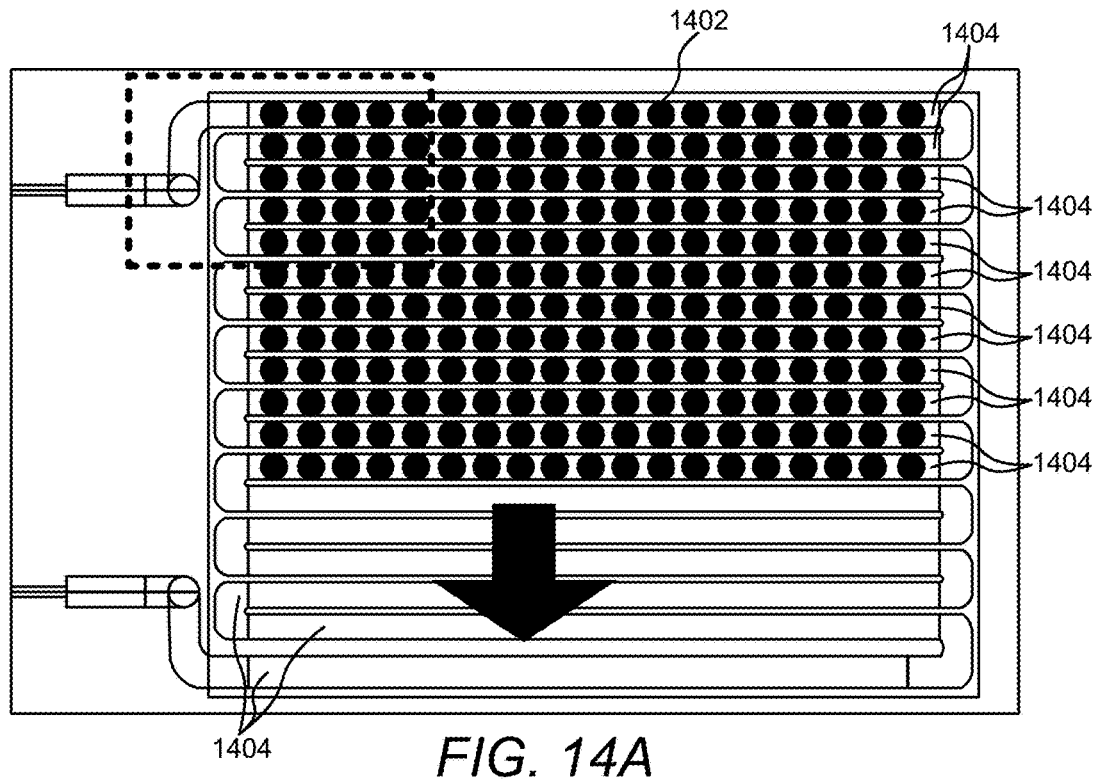
FIG. 14A depicts locations of EMASCA electrodes.
Figure 14B:
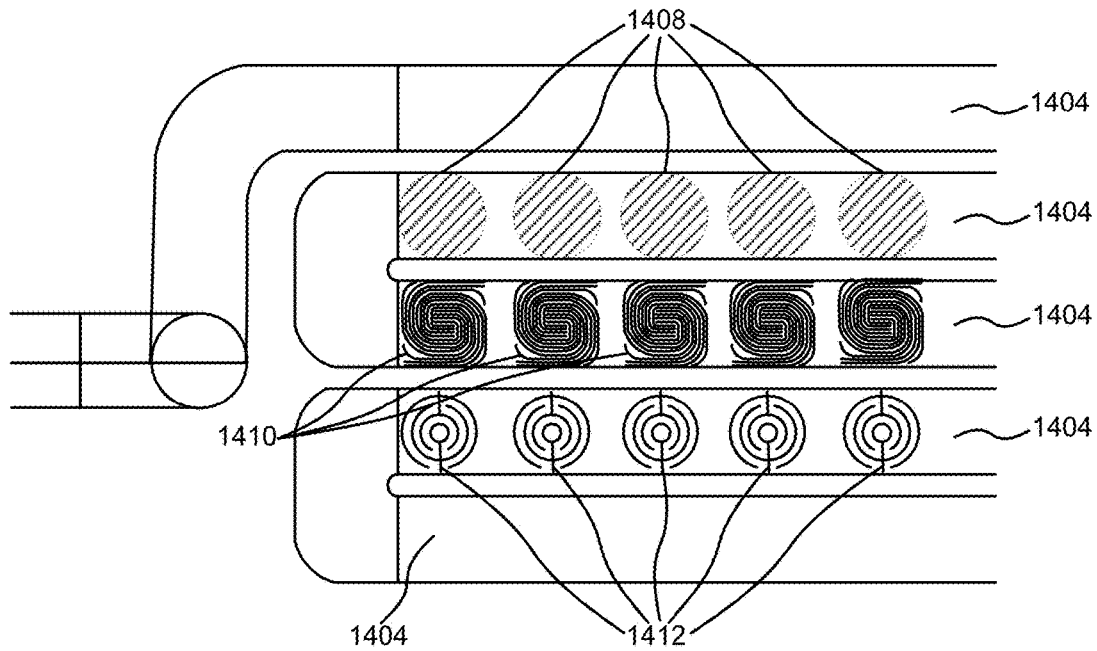
FIG. 14B depicts different types of EMASCA electrodes.

FIG. 14A shows a distribution of EMASCA electrode device embodiments 1402 along feeding channels 1404. In FIG. 14B, various EMASCA electrode devices 1408-1412 disclosed herein can be used to enable different DEP forces for different stem cell growth conditions either within a single cell culture (CC) plate or between CC plates.

Figure 15:
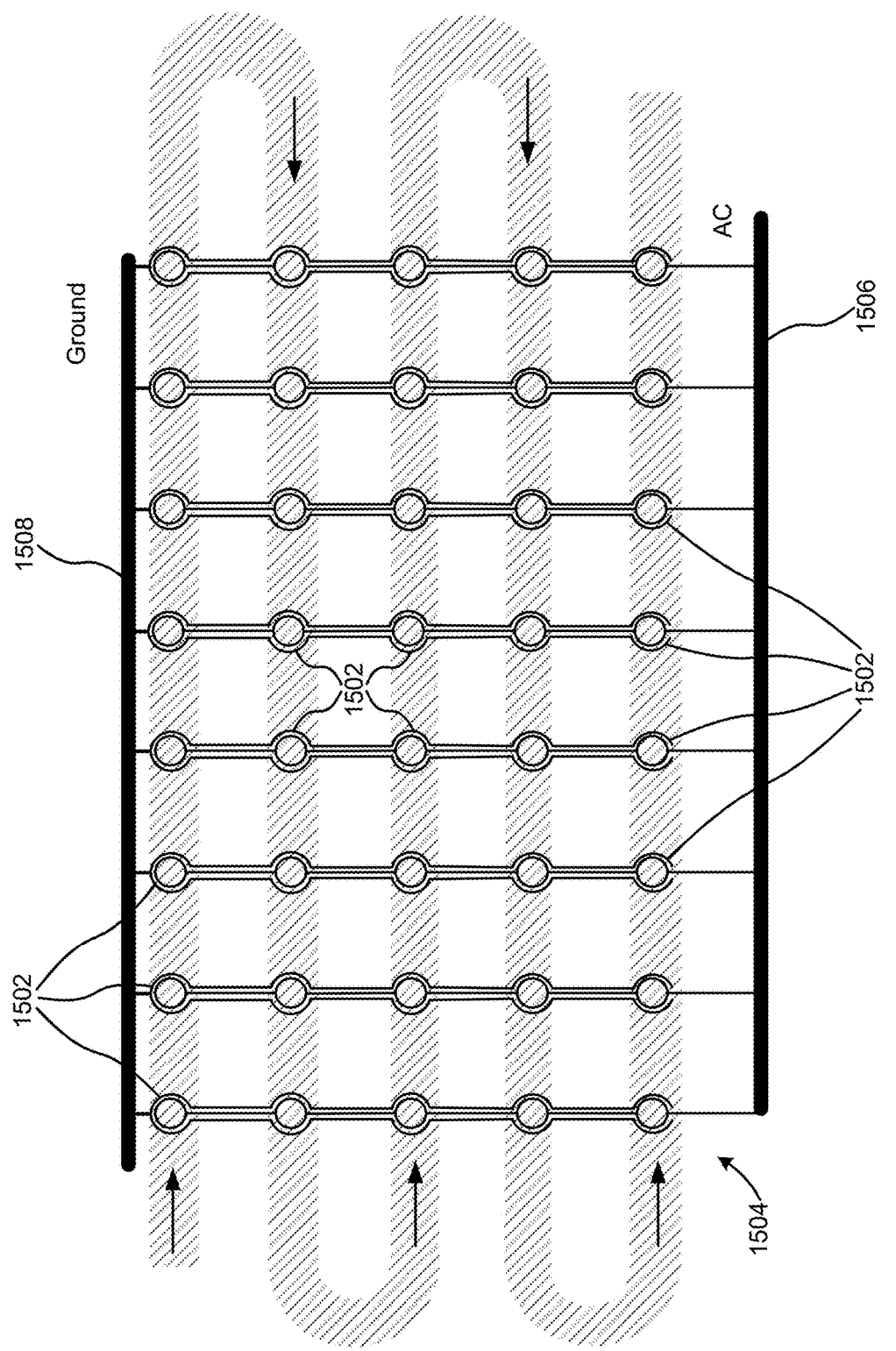
FIG. 15 depicts wire connections in system with two-electrode concentric IDE.

In one embodiment shown in FIG. 15, multiple different EMASCA electrode devices 1502 are provided to a cell culture plate 1504 with connecting wires 1506, 1508 located on the cover plate 1504. The wires 1506, 1508 can be made of transparent foil having a thickness between 10-50 µm.

In case of the EMASCA embodiment disclosed in FIG. 5 the interconnection is relatively simple, requiring two electrical leads 1506, 1508—as shown in FIG. 15.

For multi-electrode EMASCA devices, interconnecting wiring is more complex but can be readily accomplished using wiring and connection techniques well known in the art.

It is anticipated that a cell culture plate with one or more built-in EMASCA electrode devices can be integrated into automatized stem cell production and diagnostics tools, designated for bioengineering research and stem cell culture production, such as recently released Smart Cell Processing Technologies that will comprise hardware solutions in the form of equipment for culture and inspection of cells, as well as software algorithms and characterization methods.

Those of ordinary skill in the art should recognize the novelty of congruent electrodes to provide DEP forces that can manipulate cells during their culturing process, without contacting them. Their advantages include scalability and variability in cell manipulation through the disclosed embodiments.

Figure 16:
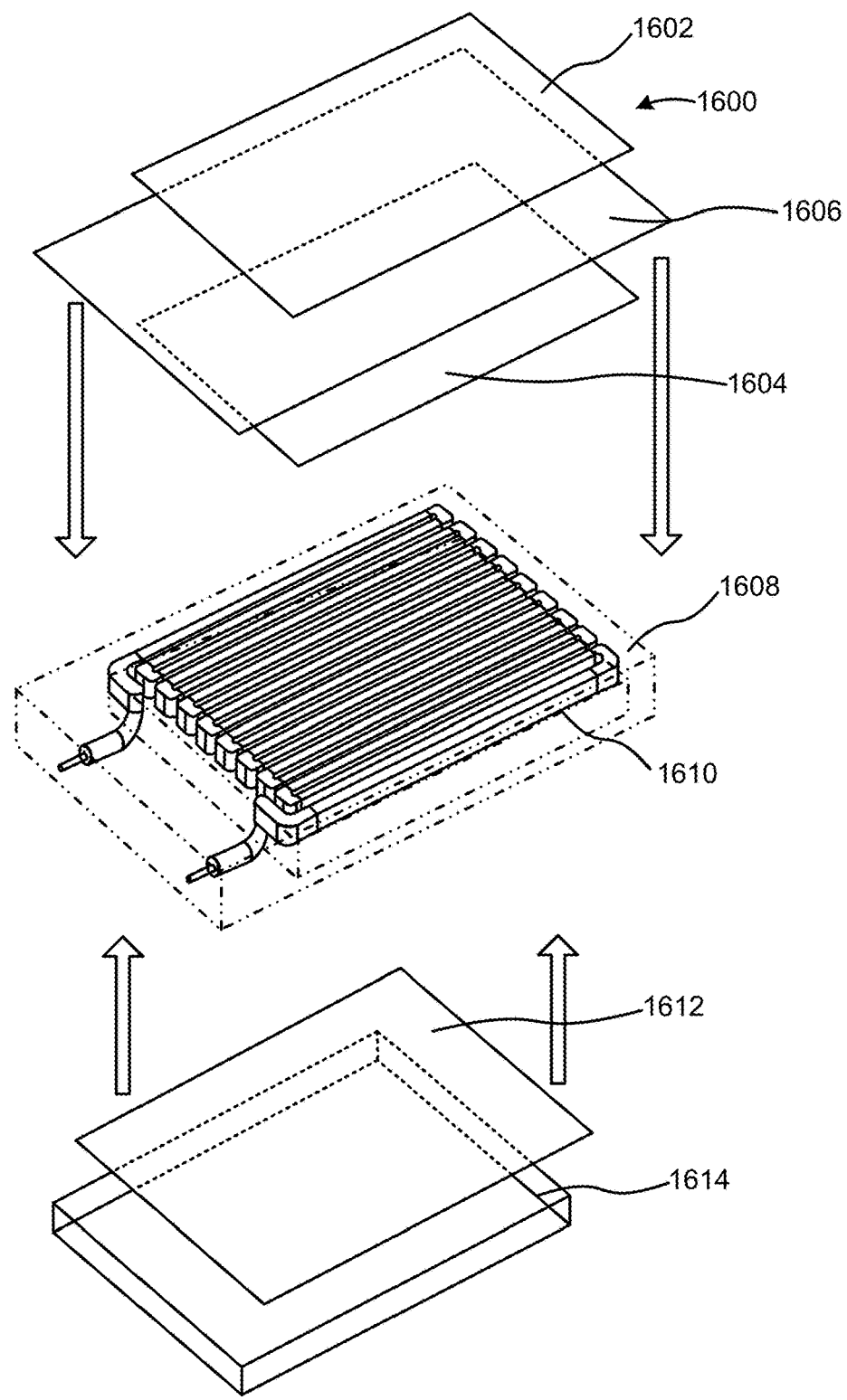
FIG. 16 is an exploded view of the depict incorporation of an EMASCA device into a cell culture plate and incubator.

Referring finally to FIG. 16, an exploded view of a channel incubator 1600 is shown. The channel incubator or simply "incubator" contains a solution in which various small particles are suspended, i.e., the particles, which can include stem cells, are suspended. The incubator is thus considered herein to also be a solution container.

The incubator 1600 includes two "sheets" 1602, 1604 of EMASCA electrode devices, which includes one or more of the electrode devices described above and shown in the figures, are attached to and thus "sandwich" a cover sheet 1606 for the top side 1608 of a long channel incubator 1610. Similarly, a third "sheet" 1612 of EMASCA electrode devices, which includes one or more electrode devices described above, and which is attached to a bottom "cover" sheet 1614 for the channel incubator 1610. A long channel incubator 1600 can thus be provided with multiple different electrode devices, which when properly energized with A.C. or D.C. currents, enables the production of DEP forces that can manipulate or position small particles, including stem cells around and through the incubator in ways that were heretofore not possible.

In addition to positioning stem cells, the subject matter disclosed herein enables cells within a colony to sort based on their electrical properties and size. Electrical permittivity is an electrical property that can vary with status of the stems cells' health and/or their internal structure.

Additional advantages and modifications will be readily apparent to those skilled in the art. The true scope of the invention is set forth in the following claims.

What is claimed is:

1. A dielectrophoresis separation apparatus comprising:
   a solution container, having at least a first side and an opposing second side, the solution container configured for containing a suspension with cells;
   the solution container including a serpentine-shaped fluid channel having an input port and output port for uploading and dispensing the cells from the fluid channel;
   a first plurality of E-field Matrix Assisted Stem Cell Alignment (EMASCA) electrode devices, operatively coupled to the first side, the EMASCA electrode devices being sized, shaped and arranged to be aligned along the serpentine-shaped fluid channel to provide electric field energy inside a volume along the fluid channel of the solution container proximate the first side of the solution container;
   the electric field energy being generated using electric signals provided to the first plurality of EMASCA electrode devices and providing forces on the cells of the suspension for dispensing cells from the fluid channel.

2. The dielectrophoresis separation apparatus of claim 1, wherein the solution container is an incubator and wherein the EMASCA electrode devices are sized, shaped and arranged along the serpentine-shaped fluid channel to provide a spatio-temporal distribution of electrical fields inside the incubator, responsive to at least an alternating current provided to the EMASCA electrode devices.

3. The dielectrophoresis separation apparatus of claim 1, wherein the EMASCA electrode devices are sized, shaped and arranged along the serpentine-shaped fluid channel to provide specific time-variant electric field patterns in particular locations of the solution container, the specific time-variant electric field patterns providing corresponding dielectrophoresis (DEP) forces in said particular locations.

4. The dielectrophoresis separation apparatus of claim 3, wherein the EMASCA electrode devices are arranged such that the cells of the suspension are subjected to the dielectrophoresis forces.

5. The dielectrophoresis separation apparatus of claim 1, wherein the EMASCA electrode devices have an actual width and a virtual width, the virtual width being an effective width, determined by electrical signals applied to said electrode devices.

6. The dielectrophoresis separation apparatus of claim 1, wherein the EMASCA electrode devices carry a plurality of A.C. signals, which differ by at least one of:
frequency;
phase; and
amplitude.

7. The dielectrophoresis separation apparatus of claim 1, wherein the first plurality of EMASCA electrode devices comprises a substantially ring-shaped electrode attached to an optically transparent, electrically permeable substrate.

8. The dielectrophoresis separation apparatus of claim 1, wherein the first plurality of EMASCA electrode devices comprises interdigitated ring-shaped electrodes attached to an electrically permeable substrate.

9. The dielectrophoresis separation apparatus of claim 1, wherein the first plurality of EMASCA electrode devices comprises a plurality of congruent, substantially spiral-shaped electrodes attached to an electrically permeable substrate.

10. The dielectrophoresis separation apparatus of claim 1, further comprising:
a second plurality of E-field Matrix Assisted Stem Cell Alignment (EMASCA) electrode devices, operatively coupled to the second side, the EMASCA electrode devices attached to the second side being sized, shaped and arranged to be aligned along the serpentine-shaped fluid channel to provide electric field energy inside the volume along the length of the fluid channel from the second side of the solution container, the electric field energy of the second plurality of EMASC electrode devices being generated using electric signals provided to the second plurality of EMASCA electrode devices.

11. A method of separating particles in a dielectrophoresis separation apparatus an having first and second opposing sides, the method comprising:
containing a suspension with particles in a serpentine-shaped fluid channel of a solution container, the serpentine-shaped fluid channel having an input port and output port for uploading and dispensing the particles from the fluid channel;
positioning a plurality of electrode devices, that are attached to a first electrically permeable substrate, on one side of the solution container and serpentine-shaped fluid channel;
arranging and sizing the electrode devices to be aligned along the serpentine-shaped fluid channel to provide electric field energy inside a volume along the fluid channel of the solution container;
applying electric energy to each electrode device of the plurality of electrode devices electrodes to provide electric field energy inside the fluid channel volume and provide forces on the particles of the suspension for dispensing particles from the fluid channel.

12. The method of claim 11, wherein the electrode devices are E-field Matrix Assisted Stem Cell Alignment (EMASCA) electrode devices.

13. The method of claim 12, wherein the EMASCA electrode devices are at least one of: ring shaped, interdigitated, or substantially spiral shaped.

14. The method of claim 11, wherein the particles are stem cells, suspended in a liquid inside the solution container.

15. The method of claim 14, wherein further comprising applying electric energy to each of the electrode devices comprises an alternating current (AC) signal having a frequency and which generates a corresponding dielectrophoretic (DEP) force on the stem cells.

16. The method of claim 15, wherein the alternating current (AC) signal has a frequency between about 10 kHz up to about 100 MHz, and wherein a DEP force generated by the AC signals directs movement of the stem cells responsive thereto.

17. The method of claim 15, wherein different alternating current (AC) signals are applied to different electrode devices of the plurality of electrode devices.

18. The method of claim 17, wherein the different alternating current (AC) signals have: a frequency, amplitude, and a phase relative to each other, at least one of the frequency, amplitude and phase being different between the different alternating current (AC) signals.

19. The method of claim 11, further comprising:
positioning another plurality of electrode devices, that are attached to a second electrically permeable substrate, on another side of the solution container and serpentine-shaped fluid channel;
arranging and sizing the electrode devices to be aligned along the serpentine-shaped fluid channel;
applying electric energy to each electrode device of the another plurality of electrode devices attached to the second electrically permeable substrate, to provide electric field energy inside the fluid channel volume and provide forces on the particles of the suspension.

20. The method of claim 19, wherein the electric energy applied to the another plurality of different electrodes is an alternating current (AC) signal having a frequency between about 10 kHz up to about 100 MHz, and wherein a DEP force generated by the AC signals directs movement of the particles responsive thereto.

* * * * *